United States Patent
Gerber

(10) Patent No.: US 9,713,706 B2
(45) Date of Patent: Jul. 25, 2017

(54) IMPLANTABLE MEDICAL ELONGATED MEMBER INCLUDING INTERMEDIATE FIXATION

(75) Inventor: Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 3371 days.

(21) Appl. No.: 11/591,448

(22) Filed: Oct. 31, 2006

(65) Prior Publication Data
US 2008/0103570 A1    May 1, 2008

(51) Int. Cl.
*A61N 1/00* (2006.01)
*A61N 1/05* (2006.01)

(52) U.S. Cl.
CPC ......... *A61N 1/0529* (2013.01); *A61N 1/0534* (2013.01); *A61N 1/0539* (2013.01); *A61N 1/0553* (2013.01); *A61N 1/0558* (2013.01); *A61N 1/057* (2013.01); *A61N 1/0536* (2013.01)

(58) Field of Classification Search
CPC .. A61N 1/0529; A61N 1/0534; A61N 1/0539; A61N 1/0553; A61N 1/0558
USPC .................................. 607/115, 122
See application file for complete search history.

(56) References Cited

U.S. PATENT DOCUMENTS

| | | | |
|---|---|---|---|
| 6,188,932 B1 | 2/2001 | Lindegren | |
| 6,510,347 B2 | 1/2003 | Borkan | |
| 6,999,819 B2 | 2/2006 | Swoyer et al. | |
| 2002/0156512 A1 | 10/2002 | Borkan | |
| 2003/0045919 A1* | 3/2003 | Swoyer et al. | 607/122 |
| 2004/0230282 A1 | 11/2004 | Cates et al. | |
| 2005/0096718 A1 | 5/2005 | Gerber et al. | |
| 2006/0004429 A1* | 1/2006 | Mrva et al. | 607/116 |
| 2006/0004430 A1 | 1/2006 | Rossing et al. | |
| 2006/0095078 A1* | 5/2006 | Tronnes | 607/2 |

FOREIGN PATENT DOCUMENTS

| | | |
|---|---|---|
| WO | 2006/076200 A2 | 7/2006 |
| WO | 2006/133445 A2 | 12/2006 |

OTHER PUBLICATIONS

Notification of Transmittal of the International Search Report and the Written Opinion of the International Searching Authority for corresponding patent application No. PCT/US2007/001939, mailed Jul. 31, 2007, 11 pages.
Reply to Written Opinion for corresponding patent application No. PCT/US2007/001939, filed Jul. 29, 2008, 17 pages.
Notification of Transmittal of the International Preliminary Report on Patentability for corresponding patent application No. PCT/US2007/001939, mailed Mar. 3, 2009, 10 pages.
(Continued)

*Primary Examiner* — Michael D Abreu
(74) *Attorney, Agent, or Firm* — Shumaker & Sieffert, P.A.

(57) ABSTRACT

An implantable medical elongated member extends between a proximal end configured to be coupled to a medical device and a distal end. The implantable elongated member includes one or more fixation elements coupled to at least a middle portion and/or a proximal portion of the elongated member in order to substantially fix a position of the elongated member to tissue at one or more intermediate points between the proximal end and the distal end of the elongated member.

26 Claims, 9 Drawing Sheets

(56) References Cited

OTHER PUBLICATIONS

Communication Pursuant to Article 94(3)EPC, from the European Patent Office for European Patent Application No. 07 749 182.7-1269, dated Dec. 4, 2009, 6 pages.
Summons to attend oral proceedings pursuant to Rule 115(1) EPC for counterpart EPC Application No. 07749182.7, dated Jun. 30, 2011, 9 pages.

* cited by examiner

IMPLANTABLE MEDICAL ELONGATED MEMBER INCLUDING INTERMEDIATE FIXATION

TECHNICAL FIELD

The invention relates to medical device systems and, more particularly, to elongated members in medical device systems.

BACKGROUND

Electrical stimulation systems may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, muscle stimulation (e.g., functional electrical stimulation (FES) of muscles) or obesity. An electrical stimulation system typically includes one or more implantable medical leads coupled to an external or implantable electrical stimulator.

The implantable medical lead may be percutaneously or surgically implanted in a patient on a temporary or permanent basis such that at least one stimulation electrode is positioned proximate to a target stimulation site. The target stimulation site may be, for example, a nerve or other tissue site, such as a spinal cord, pelvic nerve, pudendal nerve, stomach, bladder, or within a brain or other organ of a patient, or within a muscle or muscle group of a patient. The one or more electrodes located proximate to the target stimulation site may deliver electrical stimulation therapy to the target stimulation site in the form electrical signals.

Electrical stimulation of a sacral nerve may eliminate or reduce some pelvic floor disorders by influencing the behavior of the relevant structures, such as the bladder, sphincter and pelvic floor muscles. Pelvic floor disorders include urinary incontinence, urinary urge/frequency, urinary retention, pelvic pain, bowel dysfunction, and male and female sexual dysfunction. The organs involved in bladder, bowel, and sexual function receive much of their control via the second, third, and fourth sacral nerves, commonly referred to as S2, S3 and S4 respectively. Thus, in order to deliver electrical stimulation to at least one of the S2, S3, or S4 sacral nerves, an implantable medical lead is implanted proximate to the sacral nerve(s).

Electrical stimulation of a peripheral nerve, such as stimulation of an occipital nerve, may be used to mask a patient's feeling of pain with a tingling sensation, referred to as paresthesia. Occipital nerves, such as a lesser occipital nerve, greater occipital nerve or third occipital nerve, exit the spinal cord at the cervical region, extend upward and toward the sides of the head, and pass through muscle and fascia to the scalp. Pain caused by an occipital nerve, e.g. occipital neuralgia, may be treated by implanting a lead proximate to the occipital nerve to deliver stimulation therapy.

In many electrical stimulation applications, it is desirable for a stimulation lead to resist migration following implantation. For example, it may be desirable for the electrodes disposed at a distal end of the implantable medical lead to remain proximate to a target stimulation site in order to provide adequate and reliable stimulation of the target stimulation site. In some applications, it may also be desirable for the electrodes to remain substantially fixed in order to maintain a minimum distance between the electrode and a nerve in order to help prevent inflammation to the nerve and in some cases, unintended nerve damage. Securing the implantable medical lead at the target stimulation site may minimize lead migration.

SUMMARY

In general, the invention relates to an implantable medical elongated member that includes a proximal end that is configured to be coupled directly or indirectly (e.g., via an extension) to an external or implantable medical device and a distal end. The elongated member is configured to deliver a therapy, such as electrical stimulation, drug delivery, or both, from the medical device to the target therapy delivery site. The elongated member includes an elongated body that carries at least one fixation element, such as an adhesive element or a fixation structure, coupled to a middle and/or proximal portion of the elongated member. When the elongated member is implanted in a patient, the fixation element engages with surrounding tissue to substantially fix the elongated member at one or more intermediate fixation points between the proximal and distal ends of the elongated member.

Fixing the elongated member at one or more intermediate fixation points along the length of the elongated member enables the elongated member to substantially remain in place along its length, despite any movement in the region of a patient in which the elongated member is implanted. In one embodiment, the elongated member may be implanted such that there is slack between consecutive fixation points in order to help prevent the fixation elements from dislodging when the patient moves. In another embodiment, the elongated member may include elastic portions that enable the elongated member to stretch between fixation points. In yet another embodiment, the elongated member may be implanted to have slack between fixation points as well as have elastic portions. Slack and/or stretching of the elongated member may also help prevent damage or breakage of the elongated member.

In one embodiment, the invention is directed to an implantable medical elongated member configured to deliver a therapy from a medical device to a target therapy delivery site in a patient. The implantable elongated member comprises an elongated body extending between a proximal end configured to couple to the medical device and a distal end. The elongated body comprises a proximal portion adjacent to the proximal end, a distal portion adjacent to the distal end, and a middle portion located between the proximal portion and the distal portion. The proximal portion, the distal portion, and the middle portion have approximately equal lengths. The implantable medical elongated member further comprises a fixation element coupled to at least one of the proximal portion or the middle portion of the elongated member.

In another embodiment, the invention is directed toward a system comprising a medical device and an implantable elongated member. The implantable elongated member comprises an elongated body extending between a proximal end configured to couple to the medical device and a distal end. The elongated body comprises a proximal portion adjacent to the proximal end, a distal portion adjacent to the distal end, and a middle portion located between the proximal portion and the distal portion. The proximal portion, the distal portion, and the middle portion have approximately equal lengths. The implantable medical elongated member further comprises a fixation element coupled to at least one of the proximal portion or the middle portion of the elongated member.

In another embodiment, the invention is directed toward a method comprising inserting an elongated member into a body of a patient. The implantable elongated member comprises an elongated body extending between a proximal end configured to couple to the medical device and a distal end. The elongated body comprises a proximal portion adjacent to the proximal end, a distal portion adjacent to the distal end, and a middle portion located between the proximal portion and the distal portion. The proximal portion, the distal portion, and the middle portion have approximately equal lengths. The implantable medical elongated member further comprises a fixation element coupled to at least one of the proximal portion or the middle portion of the elongated member. The method further comprises advancing the elongated member to a target therapy delivery site and deploying the fixation element into tissue of the patient.

The details of one or more embodiments of the invention are set forth in the accompanying drawings and the description below. Other features, objects, and advantages of the invention will be apparent from the description and drawings, and from the claims.

DETAILED DESCRIPTION

The present invention relates to an implantable medical elongated member including one or more fixation elements disposed along a middle and/or proximal portion of the elongated member. The elongated member is configured to be directly or indirectly coupled to an implantable or external medical device to deliver a therapy from the medical device to target therapy delivery site in a patient. The location of fixation element(s) along the middle and/or proximal portion of the elongated member helps prevent the elongated member from migrating from an implantation site and helps the elongated remain substantially fixed along its length. This configuration of fixation elements may be useful, for example, when the target therapy delivery site is located a substantial distance from the medical device. In addition, intermediate fixation of the elongated member may be useful if the elongated member is routed through a region of a body of a patient that undergoes a relatively large range of movement (e.g., a back, knee, or other joints) or frequent movement. In addition to the fixation element(s) along the middle and/or proximal portion of the elongated member, the elongated member may have fixation element(s) along the distal portion.

Various embodiments of the elongated member may be applicable to different therapeutic applications. For example, the elongated member may be a stimulation lead that is used to deliver electrical stimulation to a target stimulation site, a lead extension that connects to a lead to electrically connect the lead to a medical device or a connected lead and lead extension. In another embodiment, the elongated member may be a catheter including an inner lumen that is placed to deliver a fluid, such as pharmaceutical agents, insulin, pain relieving agents, gene therapy agents, or the like from a fluid reservoir and/or pump to a target tissue site in a patient. The invention is applicable to any configuration or type of implantable elongated member that is used to deliver therapy to a site in a patient. For purposes of illustration, however, the disclosure will refer to a neurostimulation lead.

Figure 1A:
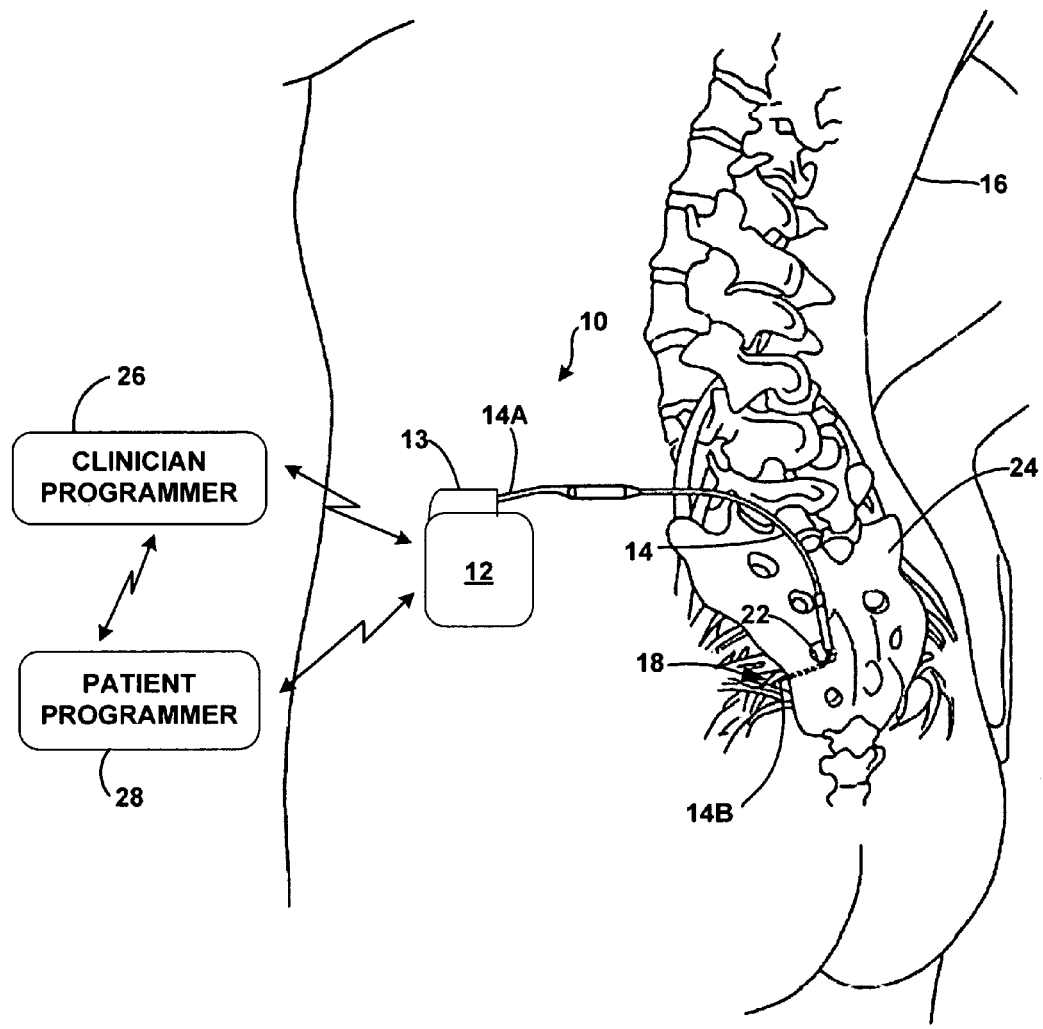
FIG. 1A is a schematic perspective view of a therapy system, which includes an electrical stimulator coupled to a stimulation lead, which has been implanted in a body of a patient proximate to a target stimulation site.

FIG. 1A is a schematic perspective view of therapy system 10, which includes electrical stimulator 12 coupled to neurostimulation lead 14. Electrical stimulator 12 may be either implantable or external. In the example of FIG. 1A, electrical stimulator 12 has been implanted in body 16 of a patient proximate to target stimulation site 18. For example, neurostimulator 12 may be subcutaneously implanted in the body of a patient (e.g., in a chest cavity, lower back, lower abdomen, or buttocks of patient 20 (not shown in FIG. 1)). Electrical stimulator 12 provides a programmable stimulation signal (e.g., in the form of electrical pulses or substantially continuous-time signals) that is delivered to target stimulation site 18 by implantable medical lead 14, and more particularly, via one or more stimulation electrodes carried by lead 14. Electrical stimulator 12 may also be referred to as a pulse or signal generator, and in the embodiment shown in FIG. 1A, electrical stimulator 12 may also be referred to as a neurostimulator. In some embodiments, lead 14 may also carry one or more sense electrodes to permit neurostimulator 12 to sense electrical signals from target stimulation site 18. Furthermore, in some embodiments, neurostimulator 12 may be coupled to two or more leads, e.g., for bilateral or multi-lateral stimulation.

As described in greater detail below, lead 14 further includes one or more fixation elements (not shown in FIG. 1A) coupled to the lead body to substantially fix a position of lead 14. Proximal end 14A of lead 14 may be both electrically and mechanically coupled to connector 13 of neurostimulator 12 either directly or indirectly (e.g., via a lead extension). In particular, conductors disposed in the lead body may electrically connect stimulation electrodes (and sense electrodes, if present) adjacent to distal end 14B of lead 14 to neurostimulator 12.

Figure 1B:
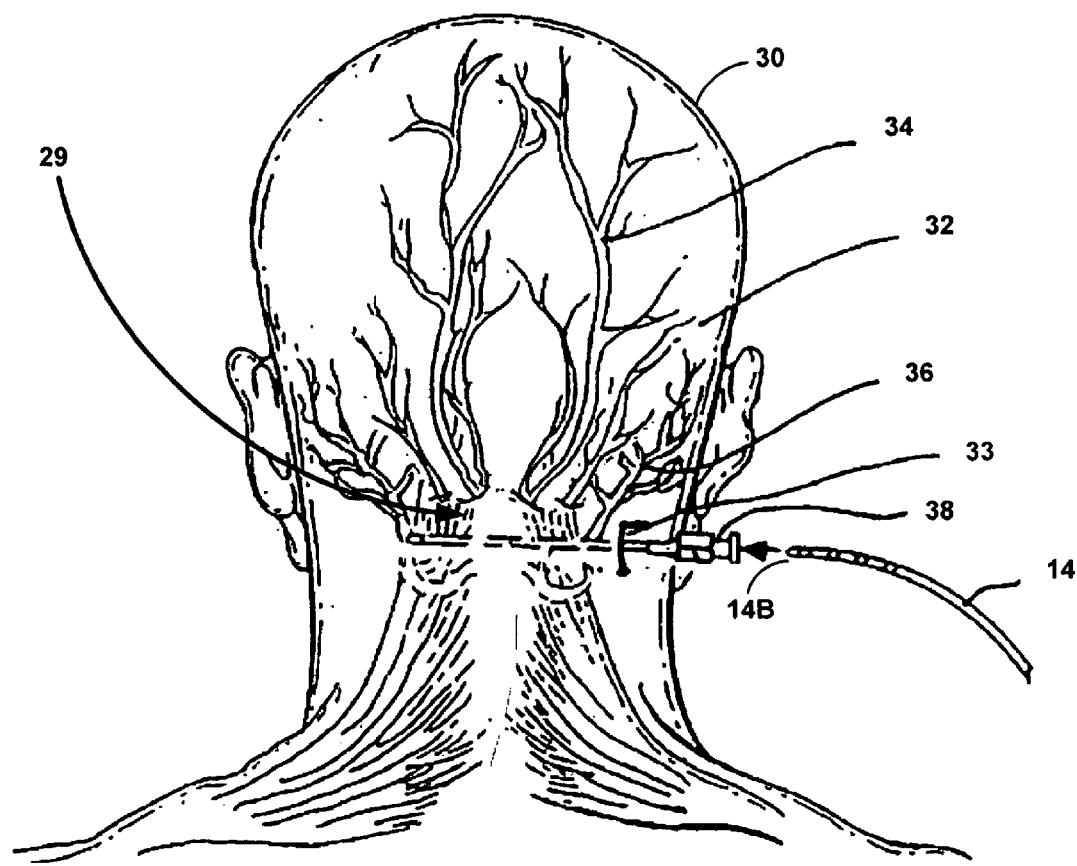
FIG. 1B illustrates the implantation of a stimulation lead at a location proximate to an occipital nerve.

In the embodiment of therapy system 10 shown in FIG. 1A, target stimulation site 18 is proximate to the S3 sacral nerve, and lead 14 has been introduced into the S3 sacral foramen 22 of sacrum 24 to access the S3 sacral nerve. Stimulation of the S3 sacral nerve may help treat pelvic floor disorders, urinary control disorders, fecal control disorders, interstitial cystitis, sexual dysfunction, and pelvic pain. Therapy system 1.0, however, is useful in other neurostimulation applications. Thus, in alternate embodiments, target stimulation site 18 may be a location proximate to any of the other sacral nerves in body 16 or any other suitable nerve in body 16, which may be selected based on, for example, a therapy program selected for a particular patient. For example, in other embodiments, therapy system 10 may be used to deliver neurostimulation therapy to a pudendal nerve, a perineal nerve, an occipital nerve (as shown in FIG. 1B) or other areas of the nervous system, in which cases, lead 14 would be implanted and substantially fixed proximate to the respective nerve.

Therapy system 10 also may include a clinician programmer 26 and a patient programmer 28. Clinician programmer 26 may be a handheld computing device that permits a clinician to program neurostimulation therapy for patient 16, e.g., using input keys and a display. For example, using clinician programmer 26, the clinician may specify neurostimulation parameters for use in delivery of neurostimulation therapy. Clinician programmer 26 supports telemetry (e.g., radio frequency telemetry) with neurostimulator 12 to download neurostimulation parameters and, optionally, upload operational or physiological data stored by neurostimulator 12. In this manner, the clinician may periodically interrogate neurostimulator 12 to evaluate efficacy and, if necessary, modify the stimulation parameters.

Like clinician programmer 26, patient programmer 28 may be a handheld computing device. Patient programmer 28 may also include a display and input keys to allow patient 16 to interact with patient programmer 28 and neurostimulator 12. In this manner, patient programmer 28 provides patient 16 with an interface for control of neurostimulation therapy by neurostimulator 12. For example, patient 16 may use patient programmer 28 to start, stop or adjust neurostimulation therapy. In particular, patient programmer 28 may permit patient 16 to adjust stimulation parameters such as duration, amplitude, pulse width and pulse rate, within an adjustment range specified by the clinician via clinician programmer 28, or select from a library of stored stimulation therapy programs.

Neurostimulator 12, clinician programmer 26, and patient programmer 28 may communicate via cables or a wireless communication, as shown in FIG. 1A. Clinician programmer 26 and patient programmer 28 may, for example, communicate via wireless communication with neurostimulator 12 using RF telemetry techniques known in the art. Clinician programmer 26 and patient programmer 28 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Therapy system 10 may also be used to provide stimulation therapy to other nerves of a patient. For example, as shown in FIG. B, lead 14 may be implanted and fixated with the one or more fixation elements proximate to an occipital region 29 of patient 30 for stimulation of one or more occipital nerves. In particular, lead 14 may be implanted proximate to lesser occipital nerve 32, greater occipital nerve 34, and third occipital nerve 36. In FIG. 1B, lead 14 is aligned to be introduced into introducer needle 38 and implanted and anchored or fixated with fixation elements proximate to occipital region 29 of patient 30 for stimulation of one or more occipital nerves 32, 34, and/or 36. A neurostimulator (e.g., neurostimulator 12 in FIG. 1A) may deliver stimulation therapy to any one or more of occipital nerve 32, greater occipital nerve 34 or third occipital nerve 36 via electrodes disposed adjacent to distal end 14B of lead 14. In alternate embodiments, lead 14 may be positioned proximate to one or more other peripheral nerves proximate to occipital nerves 32, 34, and 36 of patient 30, such as nerves branching from occipital nerves 32, 34, and 36, as well as stimulation of any other suitable nerves throughout patient 30, such as, but not limited to, nerves within a brain, stomach or spinal cord of patient 30.

Implantation of lead 14 may involve the subcutaneous placement of lead 14 transversely across one or more occipital nerves 32, 34, and/or 36 that are causing patient 30 to experience pain. In one example method of implanting lead 14 proximate to the occipital nerve, using local anesthesia, a vertical skin incision 33 approximately two centimeters in length is made in the neck of patient 30 lateral to the midline of the spine at the level of the C1 vertebra. The length of vertical skin incision 33 may vary depending on the particular patient. At this location, the skin and muscle of patient 30 are separated by a band of connective tissue referred to as fascia. Introducer needle 38 is introduced into the subcutaneous tissue, superficial to the fascia and muscle layer but below the skin. Occipital nerves 32, 34, and 36 are located within the cervical musculature and overlying fascia, and as a result, introducer needle 38 and, eventually, lead 14 are inserted superior to occipital nerves 32, 34, and 36.

Once introducer needle 38 is fully inserted, lead 14 may be advanced through introducer needle 38 and positioned to allow stimulation of the lesser occipital nerve 32, greater occipital nerve 34, third occipital nerve 36, and/or other peripheral nerves proximate to an occipital nerve. Upon placement of lead 14, introducer needle 38 may be removed. An electrical stimulator (e.g., neurostimulator 12 in FIG. 1A) that is used to deliver therapy to patient 30 via lead 14 may be implanted at any suitable location within patient 30, e.g., near the clavicle, shoulder, abdomen, buttock, etc. If the electrical stimulator is implanted at a location of substantial distance from the target therapy delivery site (e.g., target stimulation site 18 of FIG. 1A or occipital region 29 of FIG. 1B), the length of lead 14 may be long in order to connect the electrical stimulator to the target therapy delivery site.

Accurate lead placement may affect the success of occipital nerve stimulation. If lead 14 is located too deep, i.e., anterior, in the subcutaneous tissue, patient 30 may experience muscle contractions, grabbing sensations, or burning. Such problems may additionally occur if lead 14 migrates after implantation. Furthermore, due to the location of implanted lead 14 on the back of the neck of patient 30, lead 14 may be subjected to pulling and stretching that may increase the chances of lead migration. For these reasons, fixating lead 14 may be advantageous.

In alternate applications of lead 14, target stimulation site 18 may be a location proximate to any of the other sacral nerves in patient 16 or any other suitable nerve, organ, muscle, muscle group, or other tissue site in patient 16, which may be selected based on, for example, a therapy program selected for a particular patient. For example, therapy system 10 may be used to deliver electrical stimulation therapy to a pudendal nerve, a perineal nerve or other areas of the nervous system, in which cases, lead 14 would be implanted and substantially fixed proximate to the respective nerve. As further examples, lead 14 may be positioned for temporary or chronic spinal cord stimulation for the treatment of pain, for peripheral neuropathy or post-operative pain mitigation, ilioinguinal nerve stimulation, intercostal nerve stimulation, gastric stimulation for the treatment of gastric mobility disorders and obesity, muscle stimulation (e.g., functional electrical stimulation (FES) of muscles), for mitigation of other peripheral and localized pain (e.g., leg pain or back pain), or for deep brain stimulation to treat movement disorders and other neurological disorders. Accordingly, although patient 16 and target stimulation site 18 of FIG. 1A are referenced throughout the remainder of the disclosure for purposes of illustration, electrical stimulation lead 14 in accordance with the invention may be adapted for use in a variety of electrical stimulation applications, including occipital nerve stimulation, as shown in FIG. 1B with respect to patient 30.

Figure 2:
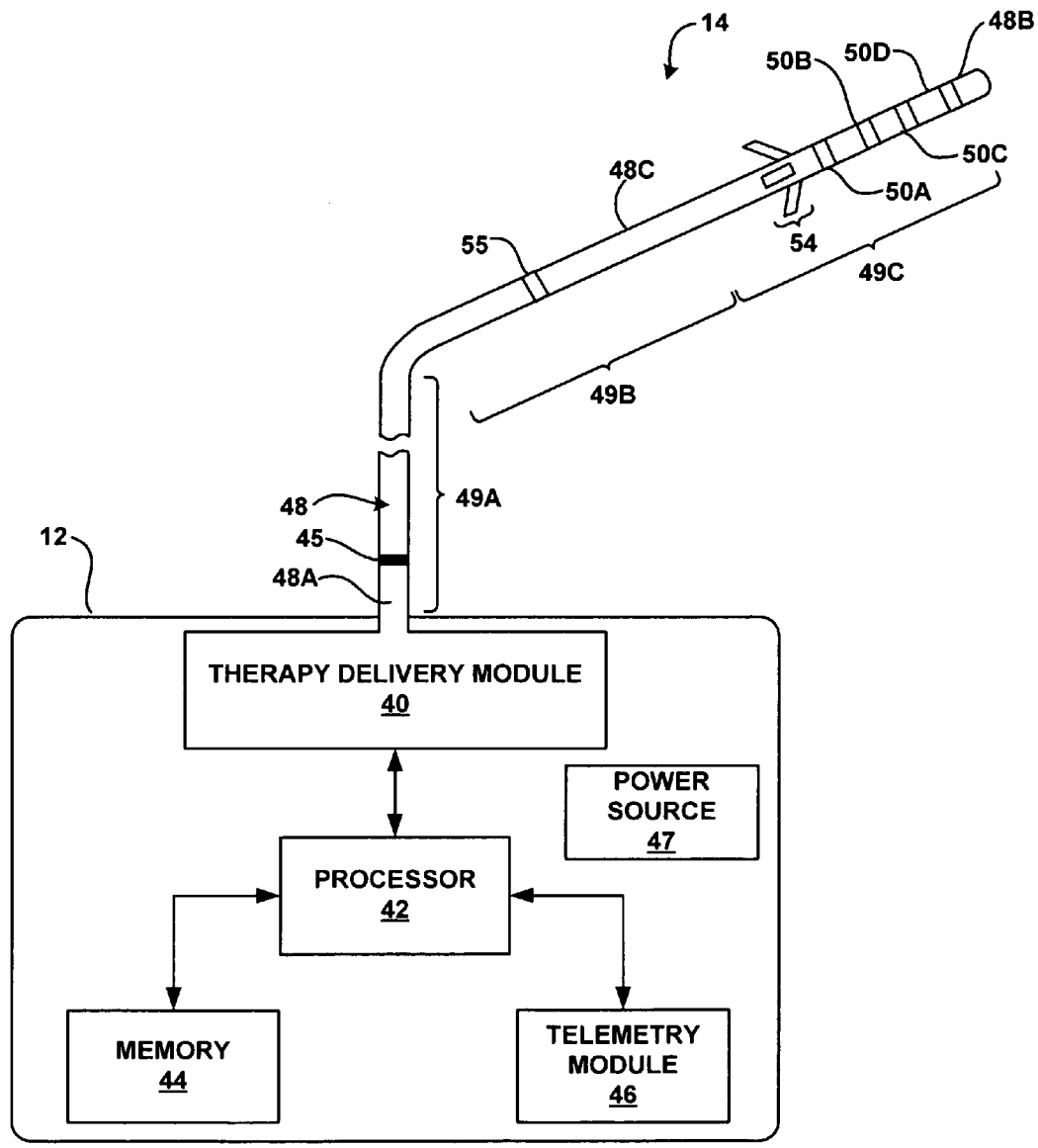
FIG. 2 is a block diagram illustrating various components of an electrical stimulator and an implantable lead.

FIG. 2 is a block diagram illustrating various components of neurostimulator 12 and an implantable lead 14. Neurostimulator 12 includes therapy delivery module 40, processor 42, memory 44, telemetry module 46, and power source 47. In some embodiments, neurostimulator 12 may also include a sensing circuit (not shown in FIG. 2). Implantable lead 14 includes lead body 48 extending between proximal end 48A and distal end 48B. Lead body 48 may be a cylindrical or may be a paddle-shaped (i.e., a "paddle" lead). Lead body 48 defines proximal portion 49A, middle portion 49B, and distal portion 49C. Proximal portion 49A is adjacent to proximal end 48A of lead body 48, distal portion 49C is adjacent to distal end 48B of lead body 48, and middle portion 49B is located between proximal and distal portions 49A and 49B. Proximal portion 49A, middle portion 49C, and distal portion 49C have approximately equal lengths (measured along a longitudinal axis of lead body 48, which extends from proximal end 48A to distal end 48B).

Electrodes 50A, 50B, 50C, and 50D (collectively "electrodes 50") are disposed on lead body 48 adjacent to distal end 48B of lead body 48. The configuration, type, and number of electrodes 50 illustrated in FIG. 2 are merely exemplary. In some embodiments, electrodes 50 may be ring electrodes. In other embodiments, electrodes 50 may be segmented or partial ring electrodes, each of which extends along an arc less than 360 degrees (e.g., 90-120 degrees) around the periphery of lead body 48. In embodiments in which lead 14 is a paddle lead, electrodes 50 may extend along one side of lead body 48. Electrodes 50 extending around a portion of the circumference of lead body 48 or along one side of a paddle lead may be useful for providing an electrical stimulation field in a particular direction/targeting a particular therapy deliver site. For example, in the electrical stimulation application shown in FIG. B, electrodes 50 may be disposed along lead body 48 such that the electrodes face toward occipital nerves 32, 34, and/or 36, or otherwise away from the scalp of patient 30. This may be an efficient use of stimulation because electrical stimulation of the scalp may not provide any or minimal useful therapy to patient 20. In addition, the use of segmented or partial ring electrodes 50 may also reduce the overall power delivered to electrodes 50 by neurostimulator 12 because of the efficient delivery of stimulation to occipital nerves 32, 34, and/or 36 (or other target stimulation site) by eliminating or minimizing the delivery of stimulation to unwanted or unnecessary regions within patient 30.

In embodiments in which electrodes 50 extend around a portion of the circumference of lead body 48 or along one side of a paddle lead, lead 14 may include one or more orientation markers 45 proximate to proximal end 14A that indicate the relative location of electrodes 50. Orientation marker 45 may be a printed marking on lead body 48, an indentation in lead body 48, a radiographic marker, or another type of marker that is visible or otherwise detectable (e.g., detectable by a radiographic device) by a clinician. Orientation marker 45 may help a clinician properly orient lead 14 such that electrodes 50 face the desired direction (e.g., toward occipital nerves 32, 34, and/or 36) within the patient. For example, orientation marker 45 may also extend around the same portion of the circumference of lead body 48 or along the side of the paddle lead as electrodes 50. In this way, orientation marker 45 faces the same direction as electrodes 50, thus indicating the orientation of electrodes 50 to the clinician. When the clinician implants lead 14 in the patient, orientation marker 45 may remain visible to the clinician.

Neurostimulator 12 delivers stimulation therapy via electrodes 50 of lead 14. Electrodes 50 are electrically coupled to a therapy delivery module 40 of neurostimulator 12 via conductors within lead body 48. More specifically, proximal end 48A of lead body 48 includes contacts (not shown) to electrically couple electrodes 50 directly to neurostimulator 12 or indirectly to neurostimulator 12 (e.g., via a lead extension). In one embodiment, an implantable signal generator or other stimulation circuitry within therapy delivery module 40 delivers electrical signals (e.g., pulses or substantially continuous-time signals, such as sinusoidal signals) to targets stimulation site 18 (FIG. 1A) via at least some of electrodes 50 under the control of a processor 42. The implantable signal generator may be coupled to power source 47. Power source 47 may take the form of a small, rechargeable or non-rechargeable battery, or an inductive power interface that transcutaneously receives inductively coupled energy. In the case of a rechargeable battery, power source 47 similarly may include an inductive power interface for transcutaneous transfer of recharge power.

The stimulation energy generated by therapy delivery module 40 may be formulated as neurostimulation energy, e.g., for treatment of any of a variety of neurological disorders, or disorders influenced by patient neurological response. The signals may be delivered from therapy delivery module 40 to electrodes 50 via a switch matrix and conductors carried by lead 14 and electrically coupled to respective electrodes 50.

Processor 42 may include a microprocessor, a controller, a DSP, an ASIC, an FPGA, discrete logic circuitry, or the like. Processor 42 controls the implantable signal generator within therapy delivery module 40 to deliver neurostimulation therapy according to selected stimulation parameters. Specifically, processor 42 controls therapy delivery module 40 to deliver electrical signals with selected amplitudes, pulse widths (if applicable), and rates specified by the programs. In addition, processor 42 may also control therapy delivery module 40 to deliver the neurostimulation signals via selected subsets of electrodes 50 with selected polarities. For example, electrodes 50 may be combined in various bipolar or multi-polar combinations to deliver stimulation energy to selected sites, such as nerve sites adjacent the spinal column, pelvic floor nerve sites, or cranial nerve sites.

Processor 42 may also control therapy delivery module 40 to deliver each signal according to a different program, thereby interleaving programs to simultaneously treat different symptoms or provide a combined therapeutic effect. For example, in addition to treatment of one symptom such as sexual dysfunction, neurostimulator 12 may be configured to deliver neurostimulation therapy to treat other symptoms such as pain or incontinence.

Memory 44 of neurostimulator 12 may include any volatile or non-volatile media, such as a RAM, ROM, NVRAM, EEPROM, flash memory, and the like. In some embodiments, memory 44 of neurostimulator 12 may store multiple sets of stimulation parameters that are available to be selected by patient 16 via patient programmer 28 (FIG. 1) or a clinician via clinician programmer 26 (FIG. 1) for delivery of neurostimulation therapy. For example, memory 44 may store stimulation parameters transmitted by clinician programmer 26 (FIG. 1). Memory 44 also stores program instructions that, when executed by processor 42, cause neurostimulator 12 to deliver neurostimulation therapy. Accordingly, computer-readable media storing instructions may be provided to cause processor 42 to provide functionality as described herein.

In particular, processor 42 controls telemetry module 46 to exchange information with an external programmer, such as clinician programmer 26 and/or patient programmer 28 (FIG. 1), by wireless telemetry. In addition, in some embodiments, telemetry module 46 supports wireless communication with one or more wireless sensors that sense physiological signals and transmit the signals to neurostimulator 12.

Migration of lead 14 following implantation may be undesirable, and may have detrimental effects on the quality of therapy delivered to a patient 16. For example, with respect to the sacral nerve stimulation application shown in FIG. 1A, migration of lead 14 may cause displacement of electrodes carried by lead 14 to a target stimulation site 18. As a result, the electrodes may not be properly positioned to deliver the therapy to target stimulation site 18, resulting in reduced electrical coupling, and possibly undermining therapeutic efficacy of the neurostimulation therapy from system 10. Substantially fixing lead 14 to surrounding tissue may help prevent lead 14 from migrating from target stimulation site 18 following implantation, which may ultimately help avoid adverse effects that may result from a migrating neurostimulation lead 14.

To that end, lead 14 further includes sutureless fixation elements 54 and 55 coupled to lead body 48 to fixate lead 14 to tissue surrounding lead 14, such as tissue within sacrum 24 in the example of FIG. 1A or tissue at occipital region 29 in the example of FIG. 1B. Fixation elements 54 and 55 may be coupled to lead body 48 via any suitable technique. In one embodiment, fixation elements 54 and 55 are each formed on lead body 48 (e.g., secured to lead body 48 via an adhesive, ultrasonic welding or otherwise). In another embodiment, fixation elements 54 and 55 are integrally formed with lead body 48 (e.g., via molding).

Fixation elements 54 are shown to be tine-like structures extending from lead body 48, while fixation element 55 is shown to be a conceptual block in FIG. 2. As described in further detail below, fixation elements 54 are located proximate to electrodes 50 to substantially fix electrodes 50 proximate to target stimulation site 18 (FIG. 1A) and fixation element 55 is at an intermediate axial location between proximal end 48A and distal end 48B of lead body 48 to substantially fix lead body 48 at a location away from electrodes 50. In particular, fixation elements 54 share an axial location on distal portion 48C of lead body 48 and fixation element 55 is located on middle portion 49B of lead body 48.

Other fixation element arrangements are contemplated in other embodiments. For example, although lead 14 includes one fixation element 55 along middle portion 49B of lead body 48 in the embodiment shown in FIG. 2, in other embodiments, lead 14 may include any suitable number of fixation elements along middle portion 49B, where each of the sets of fixation elements have different axial locations along lead body 48. In addition, lead 14 may also include one or more fixation elements along proximal portion 49A For example, in one embodiment, lead 14 may include one or more fixation elements along proximal portion 49A of lead body 48, and no fixation elements along middle portion 49B. Distal portion 49C may also include any suitable number of fixation elements, and in some embodiments, distal portion 49C may not include any fixation elements.

In one embodiment, fixation elements 54 and 55 may radially extend from less than a full outer perimeter of lead body 48. For example, a fixation element configuration extending from less than the full outer perimeter of a lead is described in commonly-assigned U.S. Patent Application Publication No. 2008/0103569 by Martin T. Gerber, entitled, "IMPLANTABLE MEDICAL ELONGATED MEMBER INCLUDING FIXATION ELEMENTS ALONG AN INTERIOR SURFACE", which was filed on Oct. 31, 2006 and is incorporated herein by reference in its entirety. Fixing lead 14 such that fixation elements 54 and 55 face away from an epidermis layer of a patient when lead 14 is implanted in the patient may be useful in an occipital nerve stimulation application, such as the one shown in FIG. 1B. For example, in the occipital nerve stimulation application of lead 14 shown in FIG. 1B, arranging fixation elements 54 and 55 along the "interior surface" (i.e., the surface facing away from the scalp of patient 30) of lead 14 may help minimize irritation to patient 30 from lead 14 and/or damage to the scalp or skin of patient 30.

Fixation elements 54 and 55 may each be any suitable size, which may depend on the particular application of lead 14. In embodiments in which fixation elements 54 and 55 are fixation structures (e.g., tines, wire-like elements, barbs, expandable elements) that are configured to extend from outer surface 48C of lead body 48, it may be desirable to select the size of or otherwise configure fixation elements 54 and 55 to fix lead 14 to a particular region of the patient, which may involve selecting the size of fixation elements 54 and 55 to accommodate the specific anatomical configuration of a region of the patient proximate to lead body 48 when lead 14 is implanted in patient 16. In addition, fixation elements 54 and 55 may be different sizes. In one embodiment, for sacral applications, fixation element 54 may be approximately sized to be expandable to a radial dimension sufficient to fix lead 14 within tissue proximate to sacral foramen 22. More specifically, fixation elements 54 and 55 may be tines, wire-like elements, or other structures that are configured to expand radially outward from lead body 48 in order to engage with surrounding tissue to help prevent migration of lead 14 from the target stimulation site. While "radially outward" is referred to throughout the disclosure, it should be understood that the expansion of fixation elements 54 and 55 may include both axial and radial components because fixation elements 54 and 55 may extend from lead body 62 at an acute angle with respect to outer surface 48C of lead body 48. Alternatively, fixation elements 54 and 55 may facilitate fixation of lead 14 within other tissue target sites, including the epidural region proximate the spine. In those cases, fixation elements 54 and 55 may be sized to expand to any of a variety of radial dimensions appropriate for engagement of tissue within the desired target therapy delivery site.

For example, fixation elements 54 and 55 may each be sized to have a radial dimension in a range of approximately 2 millimeters (mm) to 10 mm, and in one embodiment, approximately 4 mm to 6 mm, when disposed within a tissue site proximate the sacral foramen 22 (FIG. 1A) in the presence of compressive forces generated by typical tissue. In another embodiment, fixation elements 54 and 55 may facilitate fixation of lead 14 to tissue surrounding lead 14 in other locations within a patient. If lead 14 is implanted in the epidural region around the spine, for example, fixation elements 54 and 55 may each be expandable to a radial dimension in a range of approximately 6 mm to 15 mm, and in one embodiment, approximately 9 mm to 12 mm.

Sutureless fixation elements 54 and 55 are each any suitable fixation element that is capable of being implanted in patient 16 and engaging with surrounding tissue without requiring suturing of fixation elements 54 and 55 to the surrounding tissue. The sutureless fixation elements 54 and 55 minimize the invasiveness of the procedure for implanting lead 14. If each fixation element 54 and 55 was sutured to tissue within patient 16 in order to fix lead 14 at its middle portion 49B and distal portion 49C, multiple suture incisions may be required, thereby increasing the invasiveness of the implantation procedure.

Fixation elements 54 and 55 may be expanded or activated by any suitable means. In some embodiments, fixation elements may be restrained or otherwise prevented from premature fixation by a lead introducer, sheath, or other mechanism, prior to introduction into a patient. Upon implantation into the patient, fixation elements 54 and 55 may be expanded or activated by active or passive means. For example, in embodiments in which fixation elements 54 and 55 are tine-like structures, they may be expandable by elastic force such that fixation elements 54 and 55 automatically expand upon removal of the restraint mechanism. In embodiments in which fixation elements 54 and 55 (or one of fixation elements 54 or 55) are adhesive elements, withdrawing a sheath from around lead 14 may expose the adhesive elements to moisture from surrounding tissue to activate the adhesive elements. Other types of fixation elements may require additional steps in order to be expanded or activated.

In comparison to some existing methods of fixing implanted medical leads, such as suturing lead 14 to surrounding tissue, fixation elements 54 and 55 may permit implantation of lead 14 in patient 16 via a minimally invasive surgery, which may allow for reduced pain and discomfort for patient 16 relative to surgery, as well as a quicker recovery time.

Although fixation elements 54 and 55 are shown to be tine-like elements in the embodiment of FIG. 2, in other embodiments, fixation elements 54 and 55 may each be any suitable actively or passively deployed fixation element that helps prevent migration of lead 14 when lead 14 is implanted in patient 16, such as, but not limited to, one or more barbs, hooks, wire-like elements, adhesives (e.g., surgical adhesives), balloon-like fixation elements, pinning fixation elements, collapsible or expandable fixation structures, and so forth. In addition, fixation elements 54 and 55 may be formed in situ (i.e., after lead 14 is implanted in patient 16), such as by delivering a solidifying material (e.g., an adhesive or a hardenable structure material) to one or more exit ports defined by lead body 48 to form fixation elements that extend from lead body 48 to engage with surrounding tissue. Fixation elements formed in situ by flowing a solidifying material from an inner lumen within lead body 48 to an outer surface 48C of lead body 48 may be considered integrally formed or formed on lead body 48. An example of a suitable in situ formed fixation element is described in commonly-assigned U.S. Patent Application Publication No. 2008/0103578 by Martin T. Gerber, entitled "IMPLANTABLE MEDICAL ELONGATED MEMBER WITH IN SITU FORMED FIXATION ELEMENT", which was filed on Oct. 31, 2006, and is incorporated herein by reference in its entirety. Fixation elements 54 and 55 may be composed of any suitable biocompatible material, including, but not limited to, polymers, titanium, stainless steel, Nitinol, other shape memory materials, hydrogel or combinations thereof.

In some embodiments, fixation elements 54 and 55 are attached directly to lead body 48. However, in other embodiments, fixation elements 54 and 55 may not be attached directly to lead body 48, but may be carried by another apparatus that is attached to the lead body 48, such as a sleeve or mounting band. An example of a mounting band is described in commonly-assigned U.S. Pat. No. 6,999,819, entitled "IMPLANTABLE MEDICAL ELECTRICAL STIMULATION LEAD FIXATION METHOD AND APPARATUS" and issued on Feb. 14, 2006, which is hereby incorporated by reference in its entirety.

Examples of suitable hydrogel fixation elements are described in commonly assigned U.S. Patent Application Publication No. 2006/0095077, entitled "EXPANDABLE FIXATION STRUCTURES and filed on Oct. 29, 2004, U.S. Patent Application Publication No. 2006/0095078, entitled "EXPANDABLE FIXATION MECHANISM" and filed on Oct. 29, 2004, and U.S. Patent Application Publication No. 2008/0103576 by Martin T. Gerber and entitled, "IMPLANTABLE MEDICAL ELONGATED MEMBER INCLUDING HYDROGEL FIXATION MEMBER" and filed on Oct. 31, 2006.

Other suitable fixation elements may include wire-like fixation elements as described in commonly assigned U.S. Patent Application Publication No. 2005/0096718, entitled "IMPLANTABLE STIMULATION LEAD WITH FIXATION MECHANISM" and filed on Oct. 31, 2003 and commonly-assigned U.S. Patent Application Publication No. 2008/0103573 by Martin T. Gerber, entitled "IMPLANTABLE STIMULATION LEAD INCLUDING WIRE-LIKE FIXATION ELEMENTS" and filed on Oct. 31, 2006. An example of tine fixation elements is described in U.S. Pat. No. 6,999,819, entitled "IMPLANTABLE MEDICAL ELECTRICAL STIMULATION LEAD FIXATION METHOD AND APPARATUS" and filed on Nov. 9, 2001.

An example of a suitable lead including a tissue-receiving cavity to receive tissue and secure the lead to the received tissue is described in commonly-assigned U.S. Patent Application Publication No. 2008/0103577 by Martin T. Gerber, entitled "IMPLANTABLE MEDICAL ELONGATED MEMBER INCLUDING A TISSUE RECEIVING CAVITY" and filed on Oct. 31, 2006. An example of suitable balloon-like fixation elements are described in commonly-assigned U.S. Patent Application Publication No. 20080103575 by Martin T, Gerber, entitled, "IMPLANTABLE STIMULATION LEAD INCLUDING BALLOON FIXATION ELEMENT" and filed on Oct. 31, 2006. In one embodiment, lead 14 may include balloon fixation elements that are formed of a biocompatible, biodegradable material that enable the balloon fixation elements to temporarily fix lead 14 within patient 16 until sufficient fibrous ingrowth or tissue encapsulation occurs to fix lead 14. At that time, the balloon fixation elements may be engineered to degrade.

Each of the aforementioned patents and patent applications relating to suitable fixation elements for lead 14 are herein incorporated by reference in their entirety.

Figure 3:
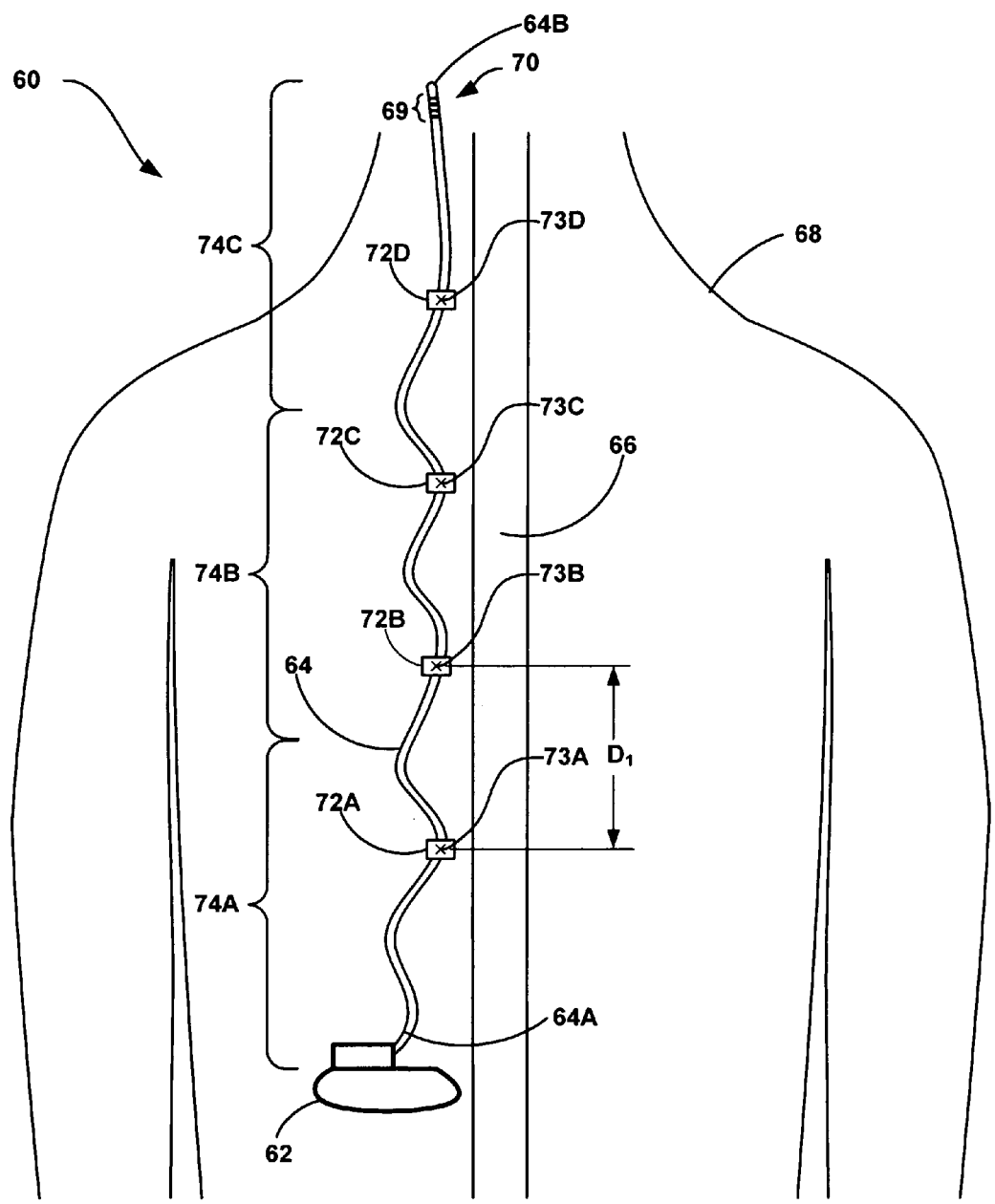
FIG. 3 is a schematic plan view of an electrical stimulation system including a lead that may be fixated to surrounding tissue to help prevent migration of the lead following implantation.

FIG. 3 is a schematic plan view of therapy system 60, which includes neurostimulator 62 coupled to neurostimulation lead 64, which extends from proximal end 64A to distal end 64B. In the illustrated embodiment, lead 64 is implanted in a back of patient 68 such that lead 64 runs along spinal cord 66 because proximal end 64A of lead 64 is coupled to neurostimulator 62 (or a lead extension that is coupled to neurostimulator 62), which is implanted in the abdomen of patient 68, and distal end 64B is implanted proximate to target therapy delivery site 70 in the neck of patient 68. Therapy delivery site 70 may be, for example, an occipital region 29 (FIG. 1B) of patient 68.

In one embodiment, at least a portion of neurostimulation lead 64 may include radio-opaque material that is detectable by imaging techniques, such as fluoroscopic imaging or x-ray imaging. This feature may be helpful for maneuvering neurostimulation lead 64 relative to target therapy delivery site 70 when implanting lead 64 within patient 68. For example, the distal end 64B of neurostimulation lead 64 may include radio-opaque material that is visible via fluoroscopic imaging. Radio-opaque markers, as well as other types of markers, such as other types of radiographic and/or visible markers, may also be employed to assist a clinician during the introduction and withdrawal of neurostimulation lead 64 from patient 68.

Lead 64 includes electrodes 69, which are located proximate to distal end 64B of lead 64 and fixation elements 72A-72D (collectively "fixation elements 72"). The particular configuration of each of fixation elements 72 is not shown in the schematic plan view of FIG. 3, but rather fixation elements are generally represented by blocks. As discussed above, fixation elements 72 may have any suitable configuration for engaging with tissue, and may include structural elements or adhesive elements.

Fixation elements 72 facilitate fixation of neurostimulation lead 64 to surrounding tissue at intermittent points 73A-D (collectively "fixation points 73") between neurostimulator 62 and target therapy delivery site 70. Lead 64 includes proximal portion 74A located adjacent to proximal end 64A, distal portion 74C located adjacent to distal end 64B, and middle portion 74B located between proximal portion 74A and distal portion 74C. Portions 74A-74C are approximately equal in length. Fixation elements 72A-72C are placed at intermittent points, i.e., at even or uneven intervals, along proximal portion 74A and middle portion 74B of lead 64 in order to anchor lead 64 at intermittent points 73 along the back of patient 68 and along the length of lead 64 (measured from proximal end 64A to distal end 64B). Lead 64 also includes fixation element 72D on distal portion 74C. Although four fixation elements are depicted on lead 64, in other embodiments, lead may include any suitable number of fixation elements along at least proximal portion 74A and/or middle portion 74B.

In cases where lead 64 is relatively long, fixing lead 64 at one or more intermittent points along lead 64 to fix lead 64 at intermediate points between proximal and distal ends 64A and 64B of lead 64 may help lead 64 remain in place despite substantial movement of patient 68 in a region in which lead 64 is implanted. For example, in the example shown in FIG. 3, lead 64 extends from the abdomen of patient 68 along spinal cord 66 in the back of patient 68 to the neck of patient 68. By placing fixation elements 72A-D intermittently along lead 64 to fix lead 64 at one or more intermediate points along the back of patient 68, lead 64 may substantially remain in place despite substantial movement of the back of patient 68. Fixing lead 64 at proximal portion 74A and/or middle portion 74B of lead 64 may also be useful in other applications in which neurostimulator 62 is implanted a relatively long distance from the tissue (e.g., nerve or muscle) to be stimulated, or applications in which lead 64 is implanted along a region of patient 68 that undergoes a relatively large range of motion or relatively frequent motion. For example, intermittent fixation of lead 64 at proximal portion 74A and/or middle portion 74B may be useful when lead 64 is implanted to extend along a joint (e.g., a knee) of a patient.

By fixing lead 64 at proximal portion 74A and/or middle portion 74B, fixation elements 72 may help reduce the amount of pulling and stretching distal portion 74C experiences as patient 68 moves by "absorbing" any tugging/pulling motion originating from proximal end 64A of lead 64. Additionally, placing a series of fixation elements 72 along proximal portion 74A and/or middle portion 74B may also help more evenly distribute the stresses that lead 64 experiences as patient 68 moves. In some embodiments, a series of intermittent fixation elements along proximal portion 74A and/or middle portion 74B, e.g., fixation elements 72A-72C, may be used to provide more secure fixation of lead 64 and/or more evenly distribute the stresses that lead 64 experiences as patient 68 moves. The fixation elements in the series, e.g., fixation elements 72A-72C, may, but need not be, approximately evenly spaced along proximal portion 74A and/or middle portion 74B of lead 64.

In addition, it may also be useful to fix distal portion 74C of lead 64 with fixation element 74D in order to fix electrodes 69 proximate to target therapy delivery site 70. Distal portion 74C of lead 64 may include any suitable number of fixation elements at any suitable location. For example, fixation element 72D may be located proximal to electrodes 69 (e.g., as shown with respect to fixation element 54 of lead 14 in FIG. 2), between electrodes 69, between electrodes 69 and distal end 64B of lead 64, or any combination thereof.

Lead 64 may be implanted in patient 68 and fixed at intermittent points 73 such that lead 64 includes some slack between the fixation points 73. For example, in the embodiment shown in FIG. 3, a length of lead 64 between fixation elements 72A and 72B may be greater than the shortest distance $D_1$ between fixation points 73A and 73B, thereby providing some slack to lead 64 between fixation points 73A and 73B. That is, when lead 64 is implanted in patient 68, lead 64 is not pulled tight between fixation points 73. The extra length between consecutive fixation points 73A-D may help prevent fixation elements 72 from dislodging when patient 68 moves. Slack in lead 64 between consecutive fixation points 73 may also help prevent damage or breakage of lead 64. The amount of slack between individual fixation points 73 may be selected to prevent lead 64 from being pulled taut between two fixation points 73 during a range of movement of patient 68.

Depending on the particular patient 68, when target therapy delivery site 70 is located in the neck of patient 68 and neurostimulator 62 is located in the abdomen of patient 68, approximately up to four inches of slack may be necessary throughout the length of lead 64 (measured from proximal end 64A to distal end 64B) to prevent lead 64 from being pulled taut between proximal end 64A and distal end 64B during a range of movement of patient 68. In an embodiment in which target therapy delivery site 70 is located in the neck of patient 68 and neurostimulator 62 is located in the buttock of patient 68, approximately six inches to eight inches of slack may be necessary throughout the length of lead 64 to prevent lead 64 from being pulled taut between proximal end 64A and distal end 64B during a range of movement of patient 68. The total amount of slack included throughout the length of lead 64 may be adjusted based on the relative locations of target therapy deliver site 70 and neurostimulator 62, as well as the size of patient 68. For example, when target therapy delivery site 70 is located in the neck of patient 68 and neurostimulator 62 is located in the buttock of patient 68, more slack is necessary than when target therapy delivery site 70 is located in the neck of patient 68 and neurostimulator 62 is located in the abdomen of patient 68. This is at least partially attributable to the fact that lead 64 traverses the hip region when neurostimulator 62 is implanted within the buttock, which introduces a greater range of movement of lead 64, thereby increasing the amount of slack required to help prevent lead 64 from being pulled tight between fixation points 73.

As described above, neurostimulation lead 64 carries a number of stimulation electrodes 69 to permit delivery of electrical stimulation to a target stimulation site such as a sacral nerve (FIG. 1A) or an occipital nerve (FIG. 1B). Accordingly, neurostimulation lead 64 includes one or more conductors to electrically couple electrodes 69 to terminals within neurostimulator 12 (FIG. 1A). While four electrodes 69 are shown in the embodiment of lead 64 of FIG. 3, in other embodiments, lead 64 may include any suitable number of electrodes.

Figure 4:
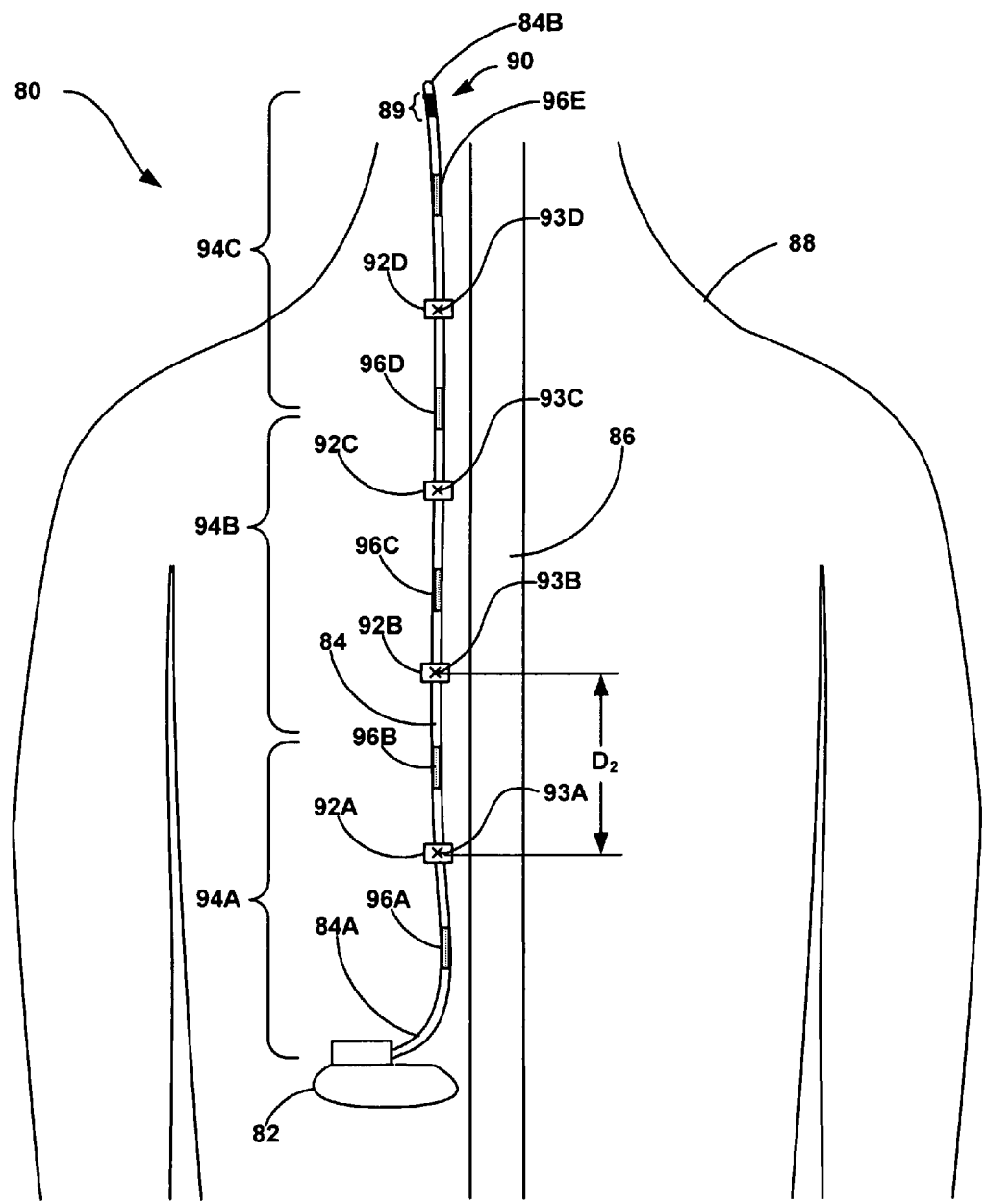
FIG. 4 is a schematic plan view of an alternative embodiment of an electrical stimulation system, which includes a lead including elastic portions.

In another embodiment, as shown in FIG. 4, a lead may be at least partially constructed of an elastic material, which may allow lead 84 to stretch between individual fixation points. FIG. 4 shows a schematic plan view of therapy system 80, which includes neurostimulator 82 coupled to neurostimulation lead 84, which has elastic portions. Alternatively, lead 84 may be coupled to a lead extension, which itself is mechanically and electrically coupled to neurostimulator 82. The lead extension may also include elastic portions. Lead 84 extends between proximal end 84A and distal end 84B. Just as with lead 64 of FIG. 3, in the embodiment shown in FIG. 4, lead 84 is implanted in patient 88 such that lead 84 traverses a back of patient 88 along spinal cord 86. Proximal end 84A of lead 84 is coupled to neurostimulator 82, which has been implanted in the abdomen of patient 88, while distal end 84B of lead 84 is located in the neck of patient 88 proximate to target therapy delivery site 90. In particular, electrodes 89, which are disposed proximate to distal end 84B of lead 84 are located proximate to target therapy delivery site 90 in order to allow neurostimulator 82 to deliver electrical stimulation to target therapy delivery site 90 via electrodes 89. In this way, lead 84 and the lead extension, if present, deliver a therapy from neurostimulator 82 to target therapy delivery site 90.

Additionally, lead 84 includes fixation elements 92A-92D (collectively "fixation elements 92") and defines proximal portion 94A located adjacent to proximal end 84A, distal portion 94C located adjacent to distal end 84B, and middle portion 94B located between proximal portion 94A and distal portion 94C. Fixation elements 92A-92C are placed at intermittent points along proximal portion 94A and middle portion 94B of lead 84 in order to anchor lead 84 at intermittent points 93A-C, respectively, along the back of patient 88. In some embodiments, especially in embodiment is which neurostimulator 82 is implanted at a substantial distance from target therapy site 90, fixating lead 84 along proximal portion 94A and/or middle portion 94B may help prevent migration of lead 84 despite substantial movement of patient 88. In the illustrated embodiment, lead 84 also includes fixation element 92D on distal portion 94C. Although four fixation elements are depicted on lead 84, any suitable number of fixation elements may be included on lead 84 on at least one proximal portion 94A and/or middle portion 94B.

In contrast to lead 64 depicted in FIG. 3, lead 84 is pulled substantially taut between fixation points 93A-D (collectively "fixation points 93"). For example, a length of lead 84 between fixation elements 92A and 92B is substantially equal to distance $D_2$ between fixation points 93A and 93B. In the embodiment illustrated in FIG. 4, lead 84 is at least partially composed of an elastic material. Specifically, at least a portion of the length of lead 84 between consecutive fixation elements 92, e.g., a portion of the length of lead 84 between fixation 92A and 92B, is composed of an elastic material such that the elastic material stretches under tensile forces and enables lead 84 to effectively increase its length between fixation points 93. Additionally, a portion of the length of lead 84 between most proximally located fixation element 92A and neurostimulator 82 may be elastic. A portion of the length of lead 84 between most distally located fixation element 92D and distal end 84B may also be elastic.

Elastic portions 96A-96E (collectively "elastic portions 96") illustrate one embodiment of lead 84. Elastic portions 96B-96D are located between each consecutive pair of fixation elements 92, elastic portion 96A is located between most proximally located fixation element 92A and neurostimulator 82, and elastic portion 96E is located between most distally located fixation element 92D and distal end 84B. Elastic portions 96B-96D between consecutive fixation elements 92 enable lead 84, and specifically the portion of lead 84 between consecutive fixation elements 92, to lengthen as patient 88 moves. This helps prevent fixation elements 92 from dislodging when patient 88 moves and may also help prevent damage to or breakage of lead 84. Although lead 84 is depicted without slack between fixation elements 92, lead 84 may, but need not, have slack between fixation elements 84. Throughout elastic portions 96B-96D, or perhaps throughout the entire length of lead 84, the electrical conductors (not shown in FIG. 4) within lead 84 that electrically couple electrodes 89 on lead 84 to neurostimulator 82 may be coiled such that successive turns of the coil are permitted to separate and relax upon axial elongation. Additionally, the entire length of lead 84 may, but need not be, elastic.

Elastic portions 96 may be formed from any suitable biocompatible and stretchable materials, including, but not limited to silicone. Elastic portions 96 are preferably formed integrally with lead 84. In embodiments in which elastic portions 96 make up an entire section of lead 84, it may also be desirable for elastic portions 96 to be composed of a dielectric material in order to electrically insulate conductors that are typically disposed within lead 84 to electrically connect neurostimulator 82 to electrodes 89.

Figure 5:
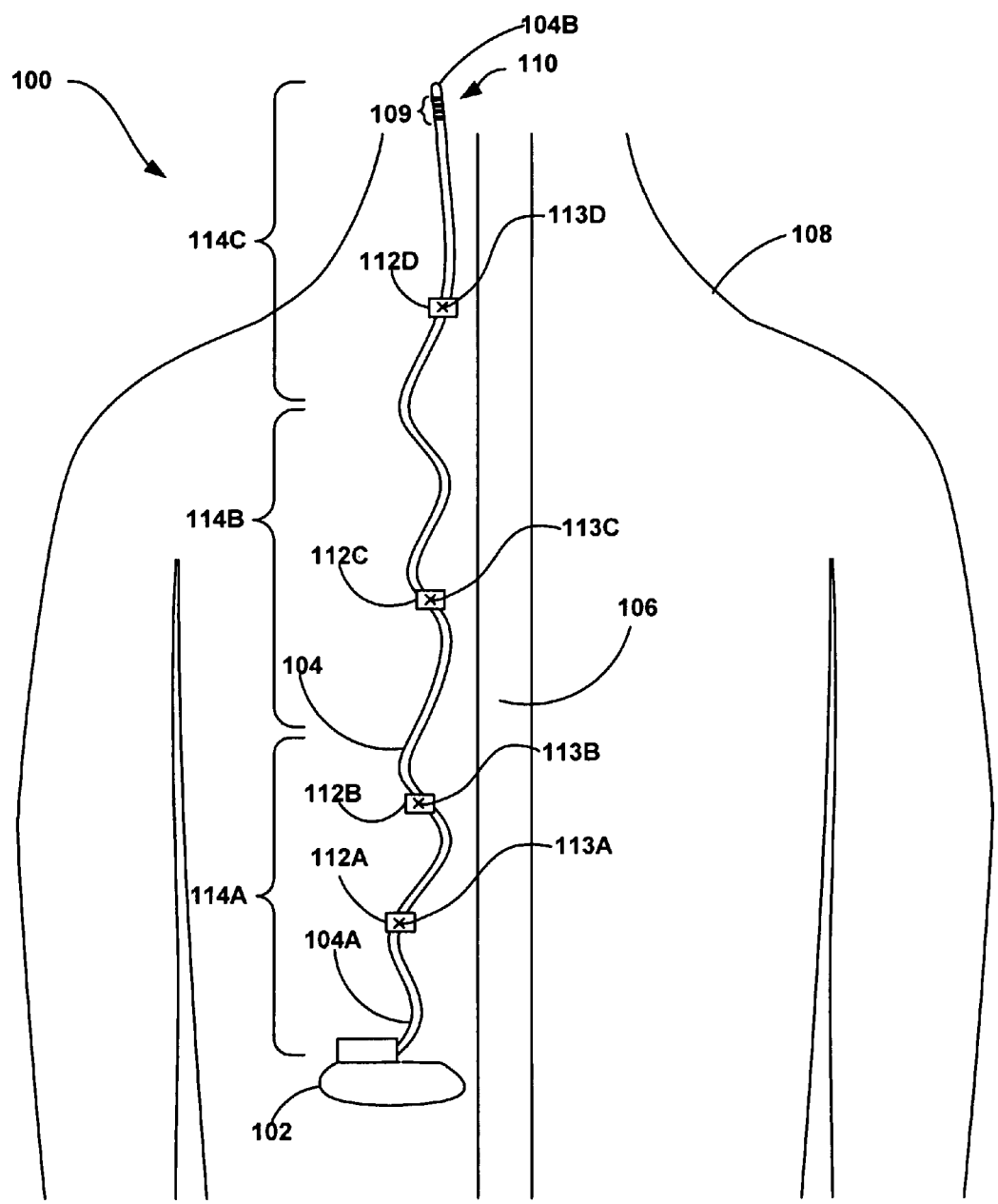
FIG. 5 is a schematic plan view of another embodiment of an electrical stimulation system including a lead that may be fixated to surrounding tissue to help prevent migration of the lead following implantation.

FIG. 5 is a schematic plan view of therapy system 100, which includes neurostimulator 102 coupled to neurostimulation lead 104 (or a lead extension that is coupled to lead 104), which extends from proximal end 104A and distal end 104B. As with leads 64 and 84 of FIGS. 3 and 4, respectively, lead 104 is implanted in a back of patient 108 such that lead 104 extends along spinal cord 106 between neurostimulator 102 and target therapy delivery site 110 in a neck of patient 108, Lead 104 includes electrodes 109 and fixation elements 112A-112D (collectively "fixation elements 112").

Fixation elements 112 are intermittently placed at intermediate points along lead 104. More particularly, lead 104 includes proximal portion 114A located adjacent to proximal end 104A, distal portion 114C located adjacent to distal end 104B, and middle portion 114B located between proximal portion 114A and distal portion 114C. Portions 114A-114C have approximately equal lengths. Fixation elements 112A-112C are placed at intermediate points along proximal portion 114A and middle portion 114B of lead 104 in order to anchor lead 104 at intermittent points 103A-C. Lead 104 also includes fixation element 112D on distal portion 114C. Although four fixation elements are depicted on lead 104, any suitable number of fixation elements may be included on lead 104 on at least one of proximal portion 114A and/or middle portion 114B.

In contrast to fixation elements 72A-72C on proximal portion 74A and middle portion 74B of lead 64 (FIG. 3), fixation elements 112A-112C are unevenly spaced with respect to each other along proximal portion 114A and middle portion 114B of lead 104. For example, in the embodiment shown in FIG. 5, fixation elements 112A and 112B are located closer together than fixation elements 112B and 112C. Thus, fixation points 113A and 113B of lead 104 are closer together than fixation points 113B and 113C. Fixation elements 112A and 112B are within the lower back of patient 108, an area in which lead 104 may experience more stretching and pulling forces due to the anatomy and range of motion of the lower back. Therefore, it may be beneficial to place fixation elements, e.g., 112A and 112B, at a higher density (i.e., closer together) in that region. In other embodiments, the spacing and density of fixation elements 112 within proximal portion 114A and/or middle portion 114B may be adjusted based on the anatomy of tissue proximate to lead 104 at other implant sites and/or based on the range of motion between fixation points 113 that fixation elements 112 withstand.

Figure 6:
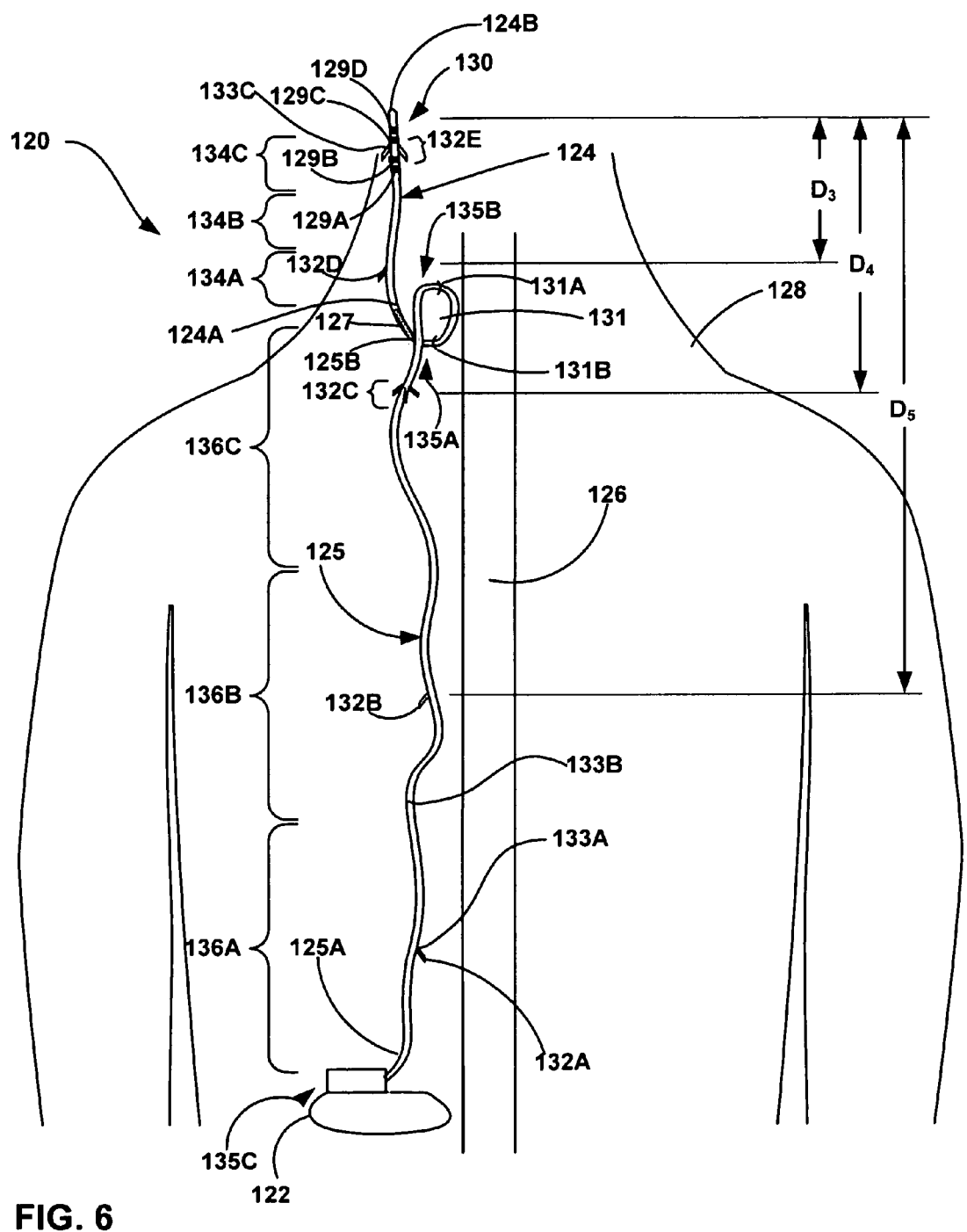
FIG. 6 is a schematic plan view of an electrical stimulation system including a lead and a lead extension, which may both be fixated to surrounding tissue to help prevent migration of the lead following implantation.

FIG. 6 is a schematic plan view of therapy system 120, which includes neurostimulator 122 coupled to neurostimulation lead 124 via lead extension 125. Lead 124 extends from proximal end 124A to distal end 124B and includes electrodes 129A-D, and lead extension 125 extends from proximal end 125A to distal end 125B. In the illustrated embodiment, lead 124 and lead extension 135 are implanted in a back of patient 128 such that lead 124 and lead extension 125 run along spinal cord 126. Proximal end 125A of lead extension 125 is coupled to neurostimulator 122, which is implanted in the abdomen of patient 128, and distal end 124B of lead 124 is implanted proximate to target therapy delivery site 130 in the neck of patient 128. For example, proximal end 125A of lead extension 125 may include a first set of electrical contacts that electrically connect to neurostimulator 122. Distal end 125B of lead extension 125 may include a second set of electrical contacts that electrically connect to a third set of electrical contacts on proximal end 124A of lead 124 to the distal end 125B of lead extension 125. The first, second, and third sets of electrical contacts may each electrically connect each of electrodes 129A-D to neurostimulator 122.

Lead 124 includes electrodes 129A-129D, which are located proximate to distal end 124B of lead 124 and fixation elements 132A-132E (collectively "fixation elements 132"). In the particular configuration illustrated in FIG. 6, fixation elements 132 are shown as tine-like elements. As discussed previously, in other embodiments, fixation elements 132 may have any suitable configuration for engaging with tissue, and may include other structural elements or adhesive elements rather than tines.

Lead 124 and lead extension 125 are coupled together using connector 127 at incision site 135A. At incision site 135A, a clinician may make a relatively small incision, such as an incision about two to about five centimeters long, couple lead 124, which has been tunneled to incision site 135A from target therapy delivery site 130, and lead extension 125, and create strain relief loop 131. Strain relief loop 131 may be formed using a portion of lead 124 and a portion of lead extension 125 such that connector 127 is included as part of strain relief loop 131. Alternatively, strain relief loop 131 may be located before or after connector 127.

Strain relief loop 131 may be formed by suturing one or more portion of lead 124 and/or lead extension 125 to patient 128. More specifically, sutures 131A and 131B may be loosely placed on strain relief loop 131. Sutures 131A and 131B may be loose to allow a portion of lead 124 and/or lead extension 125 to slide beneath sutures 131A and 131B if strain relief is needed. For example, if lead extension 125 experiences tension, strain relief loop 131 may allow extension 125 to temporary lengthen. Other suitable methods of forming strain relief loop 131 may also used.

Additionally, multiple strain relief loops may be used along the length of lead 124 and/or 125. However, since forming a strain relief loop typically requires an incision, it may be desirable to limit the use of strain relief loops to incision sites 135A-C. Incision site 135A is where an incision is made to couple lead 124 with lead extension 125, incision site 135B is where an incision is made to properly place distal end 124B at target therapy delivery site 130, and incision site 135C is where lead extension 125 is coupled to neurostimulator 122. In addition to or instead of strain relief loops, lead 124 and/or lead extension 125 may include slack between consecutive fixation points as described with respect to FIG. 3 and/or elastic portions as described with respect to FIG. 4.

Fixation elements 132 facilitate fixation of neurostimulation lead 124 to surrounding tissue at intermittent points 133A-133E (collectively "fixation points 133") between neurostimulator 122 and target therapy delivery site 130. Lead 124 includes proximal portion 134A located adjacent to proximal end 124A, distal portion 134C located adjacent to distal end 124B, and middle portion 134B located between proximal portion 134A and distal portion 134C. Portions 134A-134C are approximately equal in length. Similarly, lead extension 125 includes proximal portion 136A located adjacent to proximal end 125A, distal portion 136C located adjacent to distal end 125B, and middle portion 136B located between proximal portion 136A and distal portion 136C. Portions 136A-136C are approximately equal in length.

Both lead 124 and lead extension 125 include fixation elements along at least one of a proximal portion 124A and 125A, respectively, or a middle portion 124B and 125B, respectively, to substantially fix lead 124 and lead extension 125 to surrounding tissue. In particular, lead extension 125 includes fixation elements 132A-C at each of the proximal, middle, and distal portions 136A-C, respectively, of lead extension 125. Fixation element 132A is placed along proximal portion 136A of lead extension 125, fixation element 132B is placed along middle portion 136B, and fixation element 132C is placed along distal portion 136C. Fixation elements 132A-132C help substantially fix lead extension 125 along the length of lead extension 125 (measured from proximal end 125A to distal end 125B), and in particular, at intermittent fixation points 133A-C, respectively. Although three sets of fixation elements are depicted on lead extension 125, in other embodiments, lead extension 125 may include any suitable number of fixation elements along at least proximal portion 136A and/or middle portion 136B.

Lead 124 includes fixation elements 132D-E at its proximal and distal portions 134A and 134C, respectively, while middle portion 134B is devoid of any fixation elements. In particular, fixation element 132D is coupled to proximal portion 134A of lead 134 to fix lead 124 near strain relief loop 131. Fixation element 132E is located between individual electrodes 129B and 129C, which may help locally fix electrodes 129 of lead 124 proximate to target therapy delivery site 130. In other embodiments lead 124 may include any suitable number of fixation elements, including one or more fixation elements along proximal portion 134A and/or middle portion 134B.

The length of lead 124 typically differs depending on the particular application of electrical stimulation system 120. In some embodiments, for example, lead 124 has a length (measured from proximal end 124A to distal end 124B) in a range of approximately 20 centimeters (cm) to approximately 40 cm. Accordingly, because proximal, middle, and distal portions 134A-C of lead 124 have approximately equal lengths, in those embodiments, each one of proximal, middle, and distal portions 134A-C has a length in the range of approximately 7 cm to 13 cm. In this embodiment, a fixation element located on distal portion 134C of lead 124, such as fixation element 132D, is located within approximately 7 cm to 13 cm of distal end 124B of lead 124, and a fixation element located on proximal portion 134A or middle portion 134B of lead 124 is located more than approximately 7 cm to 13 cm away from distal end 124B. In some embodiments, a fixation element located on proximal portion 134A or middle portion 134B of lead 124 may be located more than approximately 20 cm away from distal end 124B of lead 124. Thus, in the embodiments in which lead 124 is about 20 cm to about 40 cm long, the distance between fixation elements 132D and 132E may be a range of about 19 to about 39 cm.

The length of lead extension 125 (measured from proximal end 125A to distal end 125B) may also differ depending on the particular application of electrical stimulation system 120. In some embodiments, for example, lead extension 125 has a length in a range of about 20 cm to about 100 cm. In one particular embodiment, for example, lead extension 125 has a length in a range of about 40 cm to about 50 cm. Accordingly, because proximal, middle, and distal portions 136A-C of lead extension 125 have approximately equal lengths, in those embodiments, portions 136A-C of lead extension 125 are each about 13 cm to about 17 cm long. In such an embodiment, a distance between each fixation element 132A-C may be in a range of about 14 to about 33 cm.

In the embodiment illustrated in FIG. 6, fixation element 132D located on proximal portion 134A of lead 124 is located a distance $D_3$ from a most distal electrode 129D, where distance $D_3$ is about 20 cm. Fixation element 132C is located approximately 10 cm to approximately 15 cm from fixation element 132D. Accordingly, a shortest distance $D_4$ between electrode 129D and fixation element 132C is approximately 24 cm to 48 cm. Additionally, fixation element 132B may be located along lead extension 125 such that the shortest distance $D_5$ between electrode 129D and fixation element 132B is approximately 34 cm to 60 cm. The distances $D_3$-$D_5$ are merely one embodiment of the arrangement between fixation elements 132A-E and in other embodiments, fixation elements 132A-E may be separated by any suitable distance, so long as proximal portion 136A and/or middle portion 136B of lead extension 125 includes at least one fixation element and proximal portion 134A and/or middle portion 134B of lead 124 includes at least one fixation element.

Figure 7:
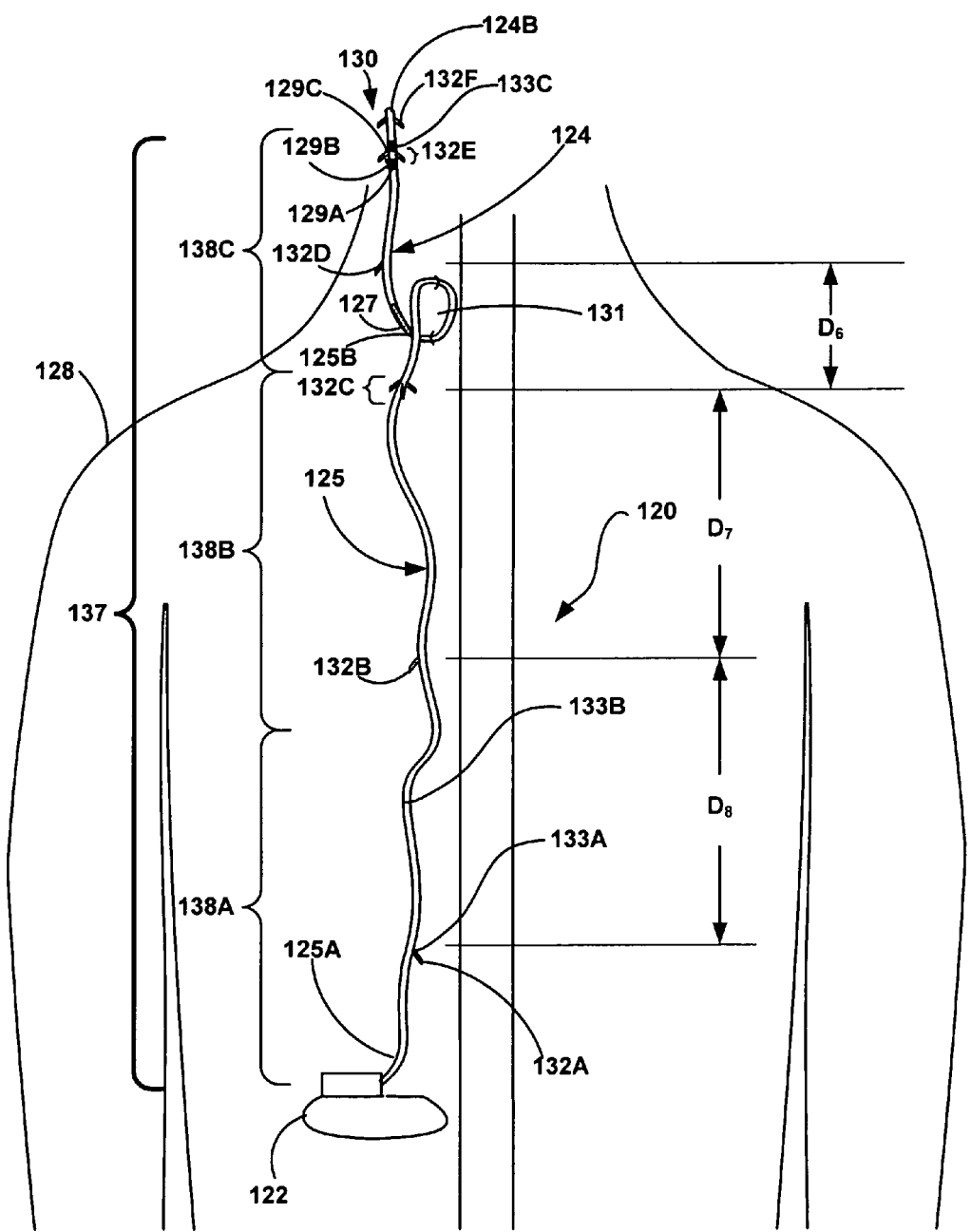
FIG. 7 is an alternative plan view of the electrical stimulation system described with respect to FIG. 6.

From another perspective, lead 124 and lead extension 125 each may effectively define a single elongated member that is used to deliver electrical stimulation therapy from neurostimulator 122 to target therapy delivery site 130. FIG. 7 illustrates a schematic plan view of therapy system 120 of FIG. 6 and illustrates an arrangement of fixation elements 132A-E about elongated member 137, which is defined by lead 124 and lead extension 125. As previously discussed, lead 124 and lead extension 125 are coupled at connector 127, effectively forming elongated member 137 extending from distal end 124B of lead 124 at target therapy delivery site 130 to proximal end 125A of lead extension 125 at neurostimulator 122.

Elongated member 137 is divided into three approximately equal portions: proximal portion 138A, middle portion 138B, and distal portion 138C. Proximal portion 138A is located adjacent to neurostimulator 122. Distal portion 138C is located adjacent to target therapy delivery site 130, and middle portion 138B is located between proximal portion 138A and distal portion 138C. While portion 138A-C are not drawn to scale in FIG. 7, distal portion 138C appears smaller relative to proximate and middle portions 138A and 138B due to extra length of distal portion 138C required to form strain relief loop 131. Of course, depending on where connector 127 is positioned, in other embodiments, strain relief loop 131 may be located within proximal or middle portions 138A-B of elongated member 137.

Fixation elements 132A-F are coupled to elongated member 137 at intermittent points along the length of elongated member 137 from proximal end 125A to distal end 124B in order to substantially fix elongated member 137 at intermediate points. In particular, fixation elements 132D-132F are located along distal portion 138C of elongated member 137, while fixation elements 132B and C are coupled to middle portion 138B, and fixation element 132A is coupled to proximal portion 138A. Although not shown in FIG. 6, FIG. 7 illustrates fixation element 132F located distal to electrodes 129 on distal portion 138C of elongated member 137. Thus, elongated member 137 includes fixation both distal to electrodes 129 and between electrodes 129.

Fixation elements 132A-F are intermittently distributed along elongated member 137. In the embodiment shown in FIG. 7, fixation elements 132A-F are not evenly distributed along the length of elongated member 137, where the length of elongated member 137 extending between proximal end 125A of lead extension 125 and distal end 124B of lead 124. For example, in the embodiment shown in FIG. 7, distance $D_6$ between fixation element 132D on distal portion 138C of elongated member 137 and fixation element 132C on middle portion 138B is about 10 to about 15 cm, while distance $D_7$ between a first fixation element 132C on middle portion 138B and a second fixation element 132B on middle portion 138B is about 10 cm to about 16 cm. Distance $D_8$ between the most proximal fixation element 132B on middle portion 138B and fixation element 132A on proximal portion 138A is also about 10 cm to about 16 cm. The distances $D_6$-$D_8$ are merely one embodiment of the arrangement between fixation elements 132A-F and in other embodiments, fixation elements 132A-F may be separated by any suitable distance, so long as proximal portion 138A and/or middle portion 138B include at least one fixation element.

Figure 8:
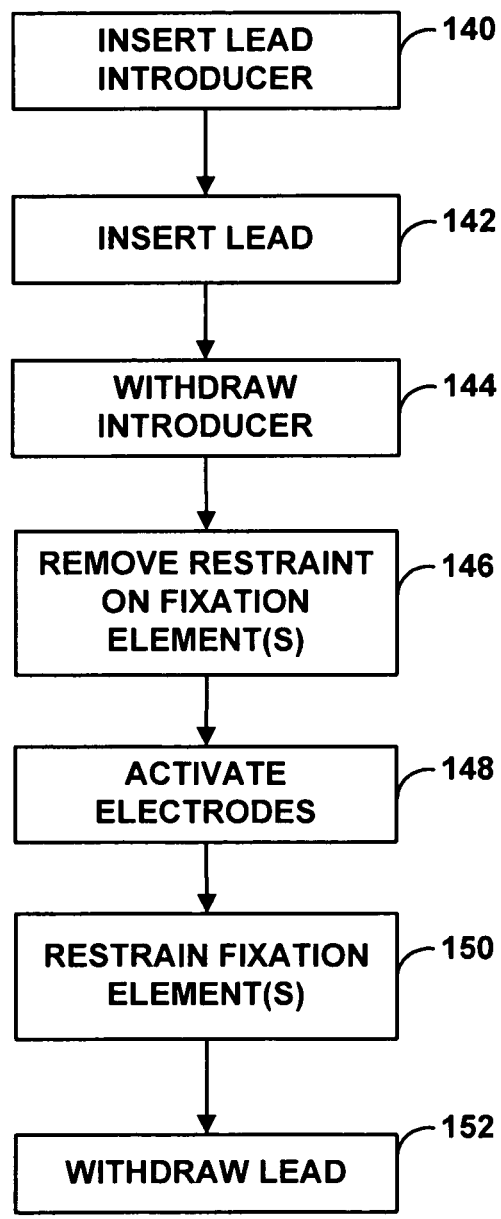
FIG. 8 is a flow diagram illustrating a process for percutaneously implanting a lead including a fixation mechanism in accordance with one embodiment of the invention.

FIG. 8 is a flow diagram illustrating a process for percutaneously implanting a lead including one or more intermittent fixation elements to fix the lead at one or more intermediate points between a proximal end and a distal end in accordance with one embodiment of the invention. While the process shown in FIG. 8 is described with respect to lead 64 of FIG. 3, in other embodiments, the lead may be, for example, any one of leads 14, 84, 104 or 124 of FIGS. 2, 4, 5, and 6 respectively, or lead extension 125 of FIG. 6 or elongated member 137 of FIG. 7. In addition, the process shown in FIG. 8 may be used to implant any suitable lead including a fixation element on a proximal or middle portion of a lead in accordance with the invention. Furthermore, while the process is described with reference to percutaneously implanting lead 64 proximate to target stimulation site 70 of FIG. 3, in other embodiments, lead 64 may be implanted proximate to any suitable target stimulation site or target therapy delivery site.

Initially, an introducer needle assembly is percutaneously inserted into patient 68 (140) and guided to target neurostimulation site 70. The needle assembly may include a needle and an introducer stylet fitted into a lumen defined by the needle. In one embodiment, the lumen has a diameter between 14 and 20 gauge to allow the needle to receive the introducer stylet. The introducer stylet may fill the lumen of the needle, preventing tissue coring. In some instances, the needle may include a straight needle for sacral implantation or a modified Tuohy needle for epidural applications, which has an opening that is angled approximately 45 degrees so that an instrument passing through the needle exits at an angle.

The lead introducer may be inserted (140) by a variety of techniques not limited to the technique described above. Lead 64 is inserted (142) into a lumen of the introducer and advanced through the introducer. Lead 64 is typically advanced through the introducer until electrodes 69 reach tissue proximate to target stimulation site 70. Meanwhile, fixation elements 72 are in an unexpanded state, undeployed state, or otherwise prevented from prematurely engaging with surrounding tissue and prematurely fixing lead 64 within patient 68. For example, a restraint mechanism may optionally be disposed around fixation elements 72 to restrain fixation elements 72 or otherwise separate fixation elements 72 from tissue of patient 68 until lead 64 is properly placed with respect to target therapy delivery site 70. In some embodiments, the restraint mechanism may be the lead introducer, a sheath other than the lead introducer, or the like. Once the neurostimulation lead reaches target stimulation site 70, the lead introducer (or sheath, if a sheath is used) is withdrawn (144). If the lead introducer is also the restraint mechanism for fixation elements 72, the act of withdrawing the lead introducer removes the restraint on fixation elements 72. Alternatively, the restraint mechanism may need to be removed after the lead introducer (146).

After electrodes 69 of neurostimulation lead 64 have been properly placed proximate to target therapy delivery site 70, electrodes 69 on lead 64 may be activated (148) to provide therapy to patient 68, e.g., by coupling a proximal end 64A of neurostimulation lead 64 to a neurostimulator 62. In one embodiment, a lead extension may be provided to couple lead 64 to neurostimulator 62. In the embodiment of therapy system 60 shown in FIG. 3, neurostimulator 62 is implanted in the abdomen of patient 68. In order to couple lead 64 to neurostimulator 62, proximal end 64A of lead 64 is tunneled along spinal cord 66 of patient 68 to reach neurostimulator 62. Lead 64 may be tunneled along spinal cord 66 prior to withdrawing lead introducer or another restraint mechanism (146). As the restraint mechanism is withdrawn, fixation elements 72 are successively deployed into tissue of patient 68.

Fixation elements 72 may be deployed from the restraint mechanism one at a time, which may provide a clinician with the opportunity to precisely and accurately place each fixation element 72 at the desired fixation point 73. For example, a clinician may withdraw the restraint mechanism proximally past fixation element 72D to deploy fixation element 72D at fixation point 73D. After the clinician places fixation element 72D at fixation point 73D, the clinician may arrange lead 64 such that fixation element 72C is placed at the desired fixation point 73C and sufficient slack, if desired, is provided between fixation points 73C and 73D. Tunneling lead 64 may provide a loose pocket that may help facilitate placing slack in lead 64. The clinician may then subsequently withdraw the restraint mechanism past fixation element 72C to deploy fixation element at fixation point 73C. The process may continue for each remaining fixation element 72.

Therapy may require that electrodes 69 of neurostimulation lead 64 be activated for only a short period of time, e.g., for trial stimulation, sometimes referred to as screening. On the other hand, therapy may require that lead 64 be implanted chronically for a number of years. In either case, it may become necessary to remove neurostimulation lead 64 from patient 68. In order to aid explantation of neurostimulation lead 64, fixation elements 72 may be restrained as they were when the lead was inserted or otherwise disengaged from surrounding tissue (150). Once fixation elements 72 are restrained, neurostimulation lead 64 may be withdrawn from patient 69 (152).

A lead including one or more fixation element on the proximal or middle portion of a lead in accordance with the invention may be useful for various electrical stimulation systems. For example, the lead may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, muscle stimulation (e.g., functional electrical stimulation (FES) of muscles) or obesity. In addition, the fixation element arrangement described herein may also be useful for fixing a catheter, such as a drug deliver catheter which delivers therapy to a target drug delivery site.

Many embodiments of the invention have been described. As previously mentioned, the distances between fixation elements for each of the embodiments are provided as embodiments of an arrangement between fixation elements of an elongated member, and are not intended to limit the scope of the present invention.

Various modifications may be made without departing from the scope of the claims. For example, the present invention further includes within its scope methods of making and using systems and leads for neurostimulation, as described herein, as well as methods of making and using elongated members for therapy systems. Also, the elongated members described herein may have a variety of therapy applications, such as fluid delivery to a target therapy delivery site or other electrical stimulation applications (e.g., sensing or delivery of cardiac electrical stimulation, including paces, pulses, and shocks). These and other embodiments are within the scope of the following claims.

The invention claimed is:

1. An implantable elongated member configured to deliver a therapy from a medical device to a target therapy delivery site in a patient, the implantable elongated member comprising:
    an elongated body extending between a proximal end configured to couple to the medical device and a distal end, wherein the elongated body comprises:
        a proximal portion including the proximal end;
        a distal portion including the distal end; and
        a middle portion located between the proximal portion and the distal portion and adjacent to the proximal portion and distal portion, wherein the proximal portion, the distal portion, and the middle portion have approximately equal lengths;
    a first fixation element coupled to the proximal portion of the elongated body;

a second fixation element coupled to the distal portion of the elongated body; and a third fixation element coupled to the middle portion of the elongated body.

2. The elongated member of claim 1, wherein the elongated body comprises a lead comprising a lead body extending between the proximal end and the distal end, and an electrode proximate to the distal end of the lead body.

3. The elongated member of claim 2, wherein the first and third fixation elements are located between the electrode and the proximal end of the lead body and the second fixation element is located between the electrode and the distal end of the lead body.

4. The elongated member of claim 2, wherein the electrode comprises an array of electrodes and the second fixation element is disposed between two electrodes of the array of electrodes.

5. The elongated member of claim 1, wherein the first fixation element is a sutureless fixation element.

6. The elongated member of claim 5, wherein the sutureless fixation element comprises at least one of an adhesive element, a tine, a flange, a balloon or a wire-like element.

7. The elongated member of claim 1, wherein the elongated body comprises a lead extension extending between the proximal end and the distal end, wherein the lead extension includes the proximal end and the distal end, and wherein the distal end is configured to couple to a lead comprising at least one electrode to electrically connect the at least one electrode to the medical device.

8. The elongated member of claim 7, wherein the lead extension has a length of about 20 centimeters to about 1 meter.

9. The elongated member of claim 1, wherein the first fixation element is integrally formed with the elongated body.

10. The elongated member of claim 1, wherein the proximal end of the elongated body is configured to directly couple to the medical device.

11. The elongated member of claim 1, wherein the third fixation element is axially displaced from the first fixation element by about ten centimeters to about sixteen centimeters.

12. The elongated member of claim 1, wherein the elongated body comprises a catheter comprising an inner lumen to deliver a fluid from the medical device to the target therapy delivery site.

13. The elongated member of claim 1, wherein the first fixation element is sized to be expandable to a radial dimension in a range of approximately 2 millimeters to 15 millimeters.

14. The elongated member of claim 1, further comprising a radio-opaque material that is detectable by fluoroscopic imaging located on at least one of the proximal, middle or distal portions of the elongated body.

15. The elongated member of claim 1, wherein at least one of the proximal, middle or distal portions of the elongated body comprises a stretchable material.

16. The elongated member of claim 1, wherein the first fixation element is located at least 20 centimeters from the distal end of the elongated body.

17. The elongated member of claim 1, wherein the elongated body comprises a lead coupled to a lead extension, the distal end of the elongated body being located on the lead and the proximal end of the elongated body being located on the lead extension.

18. The elongated member of claim 1, wherein at least one of the first, second or third fixation elements comprises at least one of an adhesive element or a tine.

19. The elongated member of claim 1, wherein the proximal and middle portions are contiguous and the middle and distal portions are contiguous.

20. A system comprising:
a medical device; and
an implantable medical elongated member comprising:
an elongated body extending between a proximal end configured to couple to the medical device and a distal end, wherein the elongated body comprises:
a proximal portion including the proximal end;
a distal portion including the distal end; and
a middle portion located between the proximal portion and the distal portion and adjacent to the proximal portion and distal portion, wherein the proximal portion, the distal portion, and the middle portion have approximately equal lengths;
a first fixation element coupled to the proximal portion of the elongated body;
a second fixation element coupled to the distal portion of the elongated body; and
a third fixation element coupled to the middle portion of the elongated body.

21. The system of claim 20, wherein the first fixation element includes at least one of an adhesive element, a tine, a flange, a balloon or a wire-like element.

22. The system of claim 20, wherein the elongated body comprises at least one of a lead comprising an electrode, a lead extension or a catheter.

23. The system of claim 20, wherein the medical device comprises at least one of a sensor to sense a parameter of a patient, an electrical stimulator or a fluid delivery device.

24. The system of claim 20, wherein at least one of the proximal, middle or distal portions of the elongated body comprises a stretchable material.

25. The system of claim 20, wherein at least one of the first, second or third fixation elements comprises at least one of an adhesive element or a tine.

26. The system of claim 20, wherein the proximal and middle portions are contiguous and the middle and distal portions are contiguous.

* * * * *